United States Patent
Hong

(10) Patent No.: US 10,611,716 B2
(45) Date of Patent: Apr. 7, 2020

(54) METHOD OF PREPARING ADIPIC ACID

(71) Applicants: Hyundai Motor Company, Seoul (KR); Kia Motors Corporation, Seoul (KR)

(72) Inventor: Chae Hwan Hong, Seoul (KR)

(73) Assignees: Hyundai Motor Company, Seoul (KR); Kia Motors Corporation, Seoul (KR)

(*) Notice: Subject to any disclaimer, the term of this patent is extended or adjusted under 35 U.S.C. 154(b) by 0 days.

(21) Appl. No.: 16/212,872

(22) Filed: Dec. 7, 2018

(65) Prior Publication Data
US 2020/0071254 A1 Mar. 5, 2020

(30) Foreign Application Priority Data
Aug. 29, 2018 (KR) .................. 10-2018-0101815

(51) Int. Cl.
| | |
|---|---|
| *C07C 51/09* | (2006.01) |
| *C07C 51/487* | (2006.01) |
| *B01J 21/04* | (2006.01) |
| *B01J 23/42* | (2006.01) |
| *C07C 51/43* | (2006.01) |

(52) U.S. Cl.
CPC .............. *C07C 51/09* (2013.01); *B01J 21/04* (2013.01); *B01J 23/42* (2013.01); *C07C 51/43* (2013.01); *C07C 51/487* (2013.01)

(58) Field of Classification Search
CPC ....... C07C 51/09; C07C 51/43; C07C 51/487; C07C 55/14; B01J 21/04; B01J 23/42
See application file for complete search history.

(56) References Cited

U.S. PATENT DOCUMENTS

| | | | | |
|---|---|---|---|---|
| 6,538,156 | B1 * | 3/2003 | Henriet | C07C 51/43 |
| | | | | 562/590 |
| 2006/0084817 | A1 * | 4/2006 | Chenault | C07D 307/33 |
| | | | | 549/292 |
| 2013/0085255 | A1 * | 4/2013 | Coudray | C07C 209/48 |
| | | | | 528/319 |
| 2014/0256982 | A1 | 9/2014 | Boussie et al. | |
| 2015/0133685 | A1 * | 5/2015 | Stubbs | C07C 1/2078 |
| | | | | 562/517 |

FOREIGN PATENT DOCUMENTS

WO   WO2017147098   * 8/2017   ............. C07C 67/03

OTHER PUBLICATIONS

White et al (Basic Energy Sciences Advisory Committee Subpanel Workshop Report, Opportunities for Catalysis in the 21st Century, 2002, pp. 1-47) (Year: 2002).*
GPP (General Process Equipment (Second Edition), Selection and Design, Ch. 12, pp. 555-582, Published 2005) (Year: 2005).*
Hashimoto (Ring-opening polyaddition of d-glucaro-1,4:6,3-dilactone with p-xylylenediamine, Makrol. Chem., Rapid Commun. 11, 393-396, Publish 1990) (Year: 1990).*
IER (Ion Exchange Resisns, Published Dec. 2009) (Year: 2009).*

* cited by examiner

*Primary Examiner* — Yevgeny Valenrod
*Assistant Examiner* — Blaine G Doletski
(74) *Attorney, Agent, or Firm* — Mintz Levin Cohn Ferris Glovsky and Popeo, P.C.; Peter F. Corless

(57) ABSTRACT

Disclosed is a method of preparing adipic acid from d-glucaro-1,4:6,3-dilactone, particularly using a rhenium catalyst and a noble metal catalyst. Further the method may include using an environmentally friendly solvent such as water. Thus, the obtained adipic acid may have high purity as a final product and economic efficiency of the preparation process may be improved.

13 Claims, 4 Drawing Sheets

METHOD OF PREPARING ADIPIC ACID

CROSS-REFERENCE TO RELATED APPLICATION

This application claims, under 35 U.S.C. § 119(a), the benefit of priority to Korean Patent Application No. 10-2018-0101815 filed on Aug. 29, 2018, the entire contents of which are incorporated herein by reference.

TECHNICAL FIELD

The present invention relates to a method of preparing adipic acid using d-glucaro-1,4:6,3-dilactone.

BACKGROUND OF THE INVENTION

Nylon-66 has been widely used as a raw material for chassis-based parts for vehicle engines. In order to manufacture the nylon-66, adipic acid and hexamethylenediamine have been used. For example, adipic acid is conventionally prepared from benzene, which may generate amounts of environmentally harmful byproducts. In the related arts, a method of preparing adipic acid using glucose, which is less harmful to the environment, has been proposed. However, the method may require complicated process such that production costs may increase and may negate economic benefits.

SUMMARY OF THE INVENTION

In preferred aspects, the present invention may provide a novel method of preparing adipic acid in an environmentally friendly manner to obtain a product having high purity and significantly improving economic efficiency of the preparation process. In the related arts, adipic acid has been prepared through a complicated synthesis process using benzene as a starting material, or a petrochemical process.

In one aspect, provided is a method of preparing adipic acid. the method may include steps of: preparing an admixture including d-glucaro-1,4:6,3-dilactone, a first solvent component and a catalyst mixture; reacting the admixture with hydrogen (H) gas; extracting the catalyst mixture from the admixture reacted with the hydrogen gas; and forming a precipitate by removing the first solvent component from the admixture from which the catalyst mixture has been extracted. Preferably, the method may further include recrystallizing the adipic acid from the precipitate using an organic solvent. Preferably, the first solvent component may include water. The first solvent component may be water.

The adipic acid may be recrystallized in a form of particle. For instance, the step of recrystallizing the adipic acid may include: adding the organic solvent to the precipitate; separating and removing an undissolved residue; and evaporating the organic solvent to obtain particles comprising the adipic acid.

The catalyst mixture may suitably include one or more selected from the group consisting of a rhenium catalyst and a noble metal catalyst. Preferably, the catalyst mixture may essentially consist of the rhenium catalyst and the noble metal catalyst.

The term "rhenium catalyst" as used herein refers to a catalyst material essentially including rhenium component, which may be any compound such as hydrates, oxides, salts, esters, and the like including rhenium metal ion or atom. For instance, the rhenium catalyst may suitably include one or more selected from the group consisting of rhenium oxide, perrhenic acid, cesium perrhenate, and ammonium perrhenate.

The term "noble metal catalyst" as used herein refers to a catalyst material essentially including noble metal component such as ruthenium (Ru), rhodium (Rh), palladium (Pd), silver (Ag), osmium (Os), iridium (Ir), nickel (Ni), platinum (Pt), and gold (Au), and the like, which may be stable and resistant to corrosion or oxidation in air (e.g., oxygen). The noble metal catalyst may include any compound such as hydrates, oxides, salts, esters, and the like including the noble metal ion or atom. Alternatively, the noble metal catalyst may include a metal component and a support including one or more selected from carbon, aluminum oxide ($Al_2O_3$), and silica.

The metal component may suitably include one or more selected from the group consisting of platinum, rhodium, palladium, and nickel.

The admixture may suitably include d-glucaro-1,4:6,3-dilactone in an amount of about 10 wt % to 20 wt % based on the total weight of the first solvent component.

The catalyst mixture may suitably include rhenium catalyst in an amount of about 5 parts by weight to 10 parts by weight and the noble metal catalyst in an amount of about 1 part by weight to 5 parts by weight based on 100 parts by weight of the d-glucaro-1,4:6,3-dilactone.

The admixture may be suitably prepared by mixing at a temperature of about 100° C. to 150° C. for a period of about 10 hr to 15 hr.

The method may further include steps of preparing the d-glucaro-1,4:6,3-dilactone. Preferably, the method may further include steps of: preparing an organic acid admixture including an organic acid or a salt thereof and a second solvent component; contacting the organic acid admixture and a cation exchange resin; separating the cation exchange resin from the organic acid admixture; preparing a composition including 1,4-dioxane and the organic acid admixture from which the cation exchange resin has been removed; and preparing d-glucaro-1,4:6,3-dilactone particles by freezing and drying the composition. The second solvent component may suitably include water, or may be water. The first solvent component and the second solvent component may be the same or different. Preferably, the first solvent component and the second solvent component may include water, or be water.

The term "organic acid" as used herein refers to an organic compound having acidic property, for example, by containing one or more functional group that can be ionized in water or an aqueous solution. Exemplary organic acid may suitably include carboxyl group (—COOH), sulfonic acids (e.g., —$SO_2OH$), alcohols (—OH) or thiol (—SH). Preferred organic acid may suitably include one or more carboxyl group, which may be ionized to produce —COO⁻ end. In certain embodiments, the organic acid containing ionized group (e.g., —COO⁻) may be in a "salt" form together with a cation such as a metal ion (e.g., Nat, $K^+$, $Ca^{2+}$ or $Mg^{2+}$) or ammonium ion ($NH_4^+$).

The organic acid or the salt thereof may include one or more potassium ions ($K^+$).

Preferably, the organic acid or the salt thereof may include potassium glucarate.

The cation exchange resin may suitably include a copolymer of styrene and divinylbenzene and include a sulfonic acid group (—$SO_3H$).

The admixture may be reacted with the hydrogen, by introducing the hydrogen gas to the mixture at a pressure of about 3 bar to 5 bar, for about 2 hr to 8 hr.

The organic solvent used in the recrystallizing may suitably include acrylonitrile.

According to various exemplary embodiments of the present invention, the method of preparing adipic acid from d-glucaro-1,4:6,3-dilactone may provide a final product having high purity and improve economic efficiency of the preparation process. In particular, an environmentally friendly process using water as a reaction solvent is provided.

DETAILED DESCRIPTION

Figure 1:
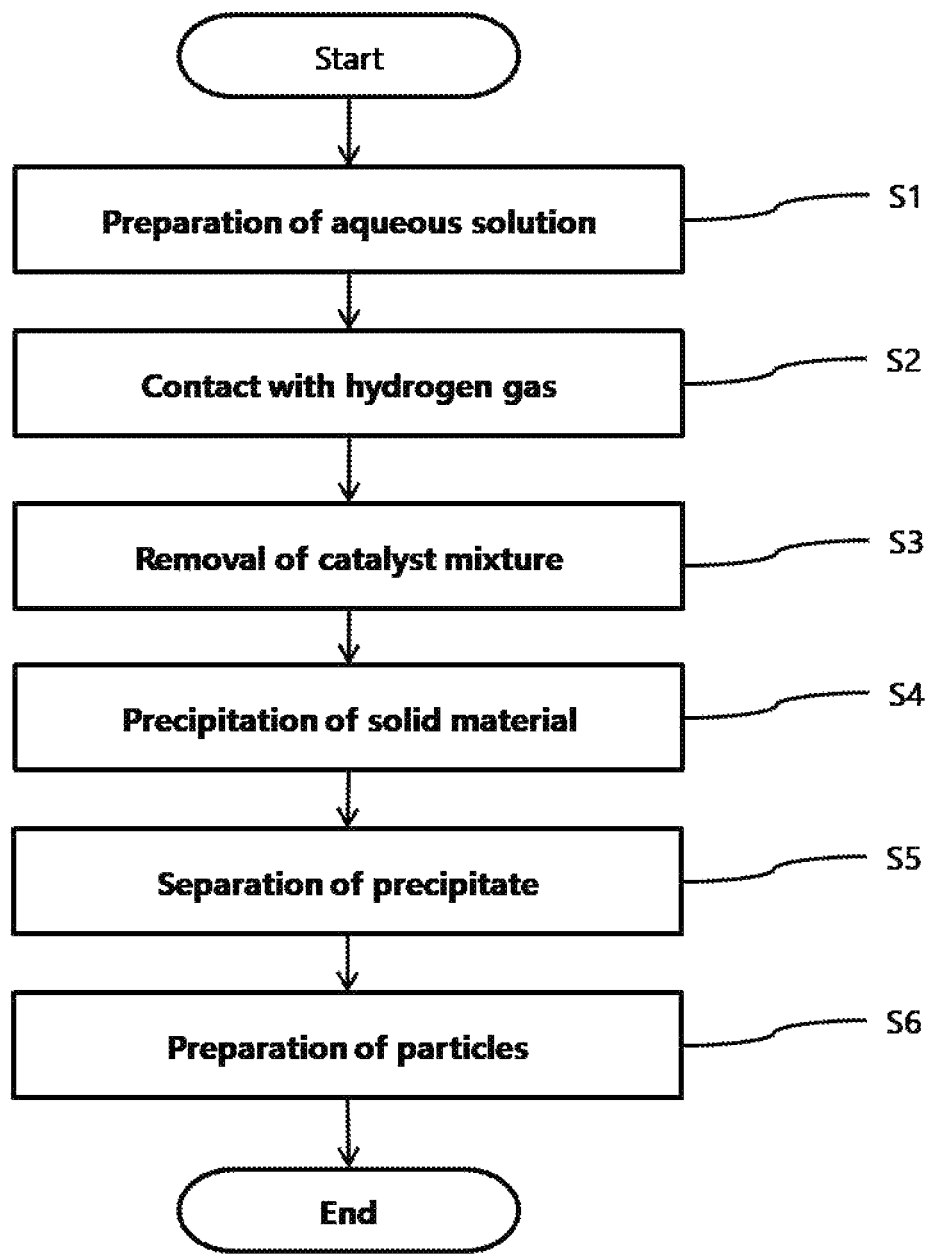
FIG. 1 shows an exemplary process of preparing adipic acid from d-glucaro-1,4:6,3-dilactone according to an exemplary embodiment of the present invention.

The above and other aspects, features and advantages of the present invention will be more clearly understood from the following preferred embodiments taken in conjunction with the accompanying drawings. However, the present invention is not limited to the embodiments disclosed herein, and may be modified into different forms. These embodiments are provided to thoroughly explain the invention and to sufficiently transfer the spirit of the present invention to those skilled in the art.

Throughout the drawings, the same reference numerals will refer to the same or like elements. For the sake of clarity of the present invention, the dimensions of structures are depicted as being larger than the actual sizes thereof. It will be understood that, although terms such as "first", "second", etc. may be used herein to describe various elements, these elements are not to be limited by these terms. These terms are only used to distinguish one element from another element. For instance, a "first" element discussed below could be termed a "second" element without departing from the scope of the present invention. Similarly, the "second" element could also be termed a "first" element. As used herein, the singular forms are intended to include the plural forms as well, unless the context clearly indicates otherwise.

It will be further understood that the terms "comprise", "include", "have", etc., when used in this specification, specify the presence of stated features, integers, steps, operations, elements, components, or combinations thereof, but do not preclude the presence or addition of one or more other features, integers, steps, operations, elements, components, or combinations thereof. Also, it will be understood that when an element such as a layer, film, area, or sheet is referred to as being "on" another element, it can be directly on the other element, or intervening elements may be present therebetween. In contrast, when an element such as a layer, film, area, or sheet is referred to as being "under" another element, it can be directly under the other element, or intervening elements may be present therebetween.

Unless otherwise specified, all numbers, values, and/or representations that express the amounts of components, reaction conditions, polymer compositions, and mixtures used herein are to be taken as approximations including various uncertainties affecting the measurements that essentially occur in obtaining these values, among others, and thus should be understood to be modified by the term "about" in all cases. Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Furthermore, when a numerical range is disclosed in this specification, the range is continuous, and includes all values from the minimum value of said range to the maximum value thereof, unless otherwise indicated. Moreover, when such a range pertains to integer values, all integers including the minimum value to the maximum value are included, unless otherwise indicated.

In the present specification, when a range is described for a variable, it will be understood that the variable includes all values including the end points described within the stated range. For example, the range of "5 to 10" will be understood to include any subranges, such as 6 to 10, 7 to 10, 6 to 9, 7 to 9, and the like, as well as individual values of 5, 6, 7, 8, 9 and 10, and will also be understood to include any value between valid integers within the stated range, such as 5.5, 6.5, 7.5, 5.5 to 8.5, 6.5 to 9, and the like. Also, for example, the range of "10% to 30%" will be understood to include any subranges, such as 10% to 15%, 12% to 18%, 20% to 30%, etc., as well as all integers including values of 10%, 11%, 12%, 13% and the like up to 30%, and will also be understood to include any value between valid integers within the stated range, such as 10.5%, 15.5%, 25.5%, and the like.

The present invention provides a novel preparation method to obtain adipic acid. Preferably, the method may include preparing adipic acid using d-glucaro-1,4:6,3-dilactone.

Hereinafter, a detailed description will be given of the present invention.

In one aspect, provided is a method of preparing adipic acid, comprising: preparing an admixture by mixing d-glucaro-1,4:6,3-dilactone, water and a catalyst mixture; reacting the admixture through contact with hydrogen (H) gas by introducing the hydrogen gas thereto; extracting the catalyst mixture from the admixture reacted with the hydrogen gas; precipitating a solid material by removing water from the admixture from which the catalyst mixture has been extracted; separating and removing an undissolved precipitate from the solution by adding the solid material to an organic solvent; and obtaining particles by evaporating the organic solvent from the solution from which the precipitate has been removed.

FIG. 1 is a flowchart showing the steps of the process of preparing adipic acid. With reference thereto, the preparation method is described below.

Preparation of Admixture (S1)

In the present invention, an admixture may be prepared by mixing d-glucaro-1,4:6,3-dilactone, a first solvent component and a catalyst mixture. Accordingly, the admixture of the initial reaction may include the d-glucaro-1,4:6,3-dilactone, the first solvent component and the catalyst mixture. Preferably, the first solvent component may suitably include a polar solvent, for example, the first solvent component may suitably include water.

Preferably, d-glucaro-1,4:6,3-dilactone may be prepared from an organic acid.

Particularly, d-glucaro-1,4:6,3dilactone may be prepared in the form of particles. The particles of the d-glucaro-1,4: 6,3dilactone may be obtained, or obtainable by a method including steps of: preparing an organic acid admixture including an organic acid or a salt thereof and a second solvent component; contacting (e.g., loading or incubating) the organic acid admixture with a cation exchange resin; separating the cation exchange resin from the organic acid admixture; preparing a composition including the organic acid admixture and 1,4-dioxane; and obtaining d-glucaro-1, 4:6,3-dilactone particles freezing and drying.

Preferably, the organic acid may be an organic acid derived from a monosaccharide such a hexose sugar monomers.

Figure 2:
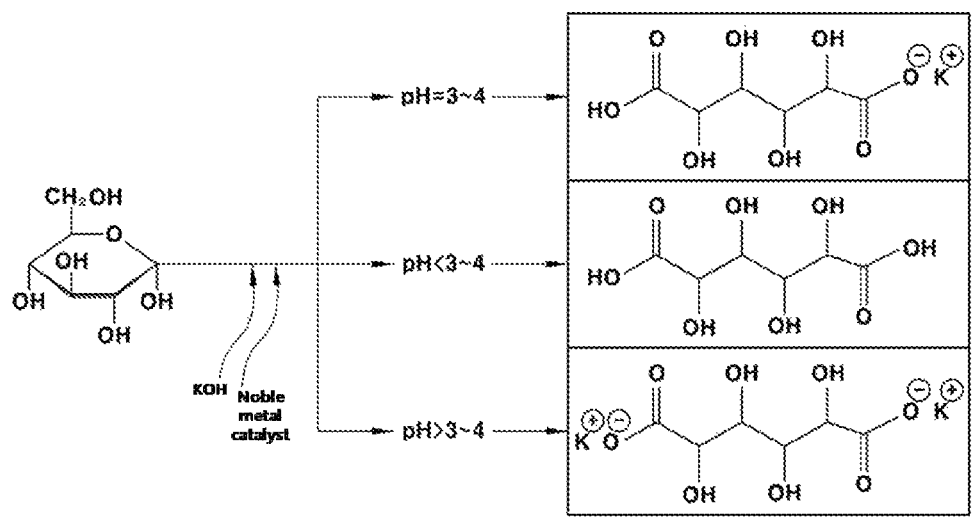
FIG. 2 shows an exemplary process of synthesizing an organic acid or salts thereof from glucose according to an exemplary embodiment of the present invention.

FIG. 2 shows an exemplary process of converting an exemplary monosaccharide (e.g., glucose) into the organic acid derivative or the salt thereof by a chemical reaction using a catalyst, such as catalytic oxidation. For instance, a reaction may be performed with glucose, a solvent such as water, potassium hydroxide (KOH) (a) and a noble metal catalyst (b) in the presence of oxygen gas, which may induce an oxidation reaction, and thus an organic acid salt or derivatives thereof may be obtained. Various exemplary organic acid may be obtained under various the hydrogen ion concentration of the reaction conditions. For example, at a pH of about 3 to 4, glucaric acid including a potassium cation ($K^+$) may be formed as a salt. When the pH is less than 3, glucaric acid derivative without a potassium cation ($K^+$) may be formed. When the pH is greater than 4, glucaric acid including one or more potassium cations ($K^+$) which may be present at both ends of the organic acid may be obtained. Preferably, the organic acid may suitably include glucaric acid (potassium glucarate), in which a potassium cation ($K^+$) may be present in the form of a salt at only one end thereof.

The cation exchange resin may be a strongly acidic cation exchange resin. Preferably, the cation exchange resin may include one or more copolymers including styrene and divinylbenzene and include a sulfonic acid group (—$SO_3H$) as an exchange group.

The d-glucaro-1,4:6,3-dilactone thus prepared may be mixed with the solvent such as water, together with the catalyst mixture, for preparing an admixture.

The catalyst mixture may include one or more selected from the group consisting of a rhenium catalyst, and a noble metal catalyst. Preferably, the rhenium catalyst may remove a hydroxyl group (—OH) positioned at both sides of d-glucaro-1,4:6,3-dilactone through reaction with d-glucaro-1,4: 6,3-dilactone. For example, a bond connected to the hydroxyl group may be broken and a double bond may be formed. The noble metal catalyst may convert the double bond formed by the rhenium catalyst into a single bond. Accordingly, the catalyst mixture may include rhenium catalyst and the noble metal catalyst for the conversion of d-glucaro-1,4:6,3-dilactone into adipic acid.

The catalyst components of the catalyst mixture may be added simultaneously the first solvent component (e.g., water), or may be added at different times or sequentially, which may be determined depending on the purpose and the experimental conditions.

The rhenium catalyst may suitably include one or more selected from the group consisting of rhenium oxide, perrhenic acid, cesium perrhenate, and ammonium perrhenate. Preferably, the rhenium catalyst may include ammonium perrhenate ($NH_4ReO_4$).

The noble metal catalyst may include a metal component that may be loaded on a support including one or more selected from the group consisting of carbon, aluminum oxide ($Al_2O_3$), and silica. Preferably, the metal component may suitably include one or more selected from the group consisting of platinum, rhodium, palladium, and nickel. Preferably, the noble metal catalyst may be provided in a form (Pt—$Al_2O_3$) in which a platinum element may be loaded on an aluminum oxide support. The aluminum oxide support may be acidic and promote or facilitate the reaction.

The catalyst mixture may suitably include ammonium perrhenate ($NH_4ReO_4$) and platinum-aluminum oxide (Pt—$Al_2O_3$).

The first solvent component may suitably include water, or be water. When the first solvent component include alcohol, such as ethanol or methanol other than water, or a solvent out of the pH range of 6 to 8, the reaction between d-glucaro-1,4:6,3-dilactone and the catalyst mixture may not occur or a desired product may not be obtained, and or other byproduct may be produced.

The admixture may include d-glucaro-1,4:6,3-dilactone in an amount of about 10 wt % to 20 wt % based on the total weight of the admixture and the first solvent component (e.g., water) and thus d-glucaro-1,4:6,3-dilactone may be dissolved. When the amount of d-glucaro-1,4:6,3-dilactone is out of the predetermined range, bather (e.g., film) properties for mass transfer to surface active sites of the catalysts of the catalyst mixture may be increased, thus deteriorating reaction characteristics upon preparation of the admixture.

The catalyst mixture may suitably include the rhenium catalyst in an amount of 5 parts by weight to 10 parts by weight and the noble metal catalyst is added in an amount of 1 part by weight to 5 parts by weight, based on 100 parts by weight of d-glucaro-1,4:6,3-dilactone. When the amount of the rhenium catalyst is out of the predetermined range, solubility in the solvent may decrease and the bather (e.g., film) properties for material transfer may be increased, and thus reaction characteristics may deteriorate. When the amount of the noble metal catalyst is out of the predetermined range, acidity of the first solvent component may not be suitably controlled, and thus the reaction yield may decrease.

Preferably, when the admixture is prepared by mixing d-glucaro-1,4:6,3-dilactone, the catalyst mixture and the first solvent component including water, the admixture may be formed by mixing at a temperature of about 100° C. to 150° C. and the for about 10 hr to 15 hr. When the mixing temperature is less than about 100° C., reactivity may decrease due to catalyst deactivation. When the mixing temperature is greater than about 150° C., the activity of the noble metal catalyst may decrease due to excessive heat generation, and thus total reactivity may decrease. Further, when the mixing time is out of the predetermined range, the reaction may not sufficiently occur, thus producing impurities.

Contact with Hydrogen Gas (S2)

After the admixture is obtained in the previous step (S1), a reaction may be performed hydrogenation, for example, by contacting the admixture with hydrogen (H) gas. Preferably, the hydrogen gas may be introduced to a reactor containing the reaction components (e.g., admixture and catalyst).

In this step (S2), the introduced hydrogen may convert double bonds formed in the previous step (S1) into single bonds. The pressure and the introduction time of hydrogen gas introduced in this step (S2) may be maintained or adjusted at a predetermined range.

Preferably, the pressure of hydrogen gas that may be introduced to the reaction may range from about 3 bar to about 5 bar. The introduction time of hydrogen gas, or the reaction time, may range from about 2 hr to about 8 hr. When the pressure of hydrogen gas is less than about 3 bar, hydrogenation efficiency may drastically decrease. When the pressure of hydrogen gas is greater than about 5 bar, abnormal reaction may occur, thus increasing the amount of impurities. Further, when the reaction time is less than about 2 hr, the reaction yield may decrease. When the reaction time is greater than about 8 hr, impurities may be generated.

Removal of Catalyst Mixture (S3)

After sufficient hydrogenation with hydrogen gas in the previous step (S2), the catalyst mixture may be extracted and removed from the admixture. Preferably, the reaction temperature may be decreased to room temperature, and the noble metal catalyst may be removed through a filtering process.

For example, a portion of the catalyst mixture removed in this step (S3) may suitably include the noble metal catalyst and the remaining portion of the catalyst mixture may suitably include the rhenium catalyst.

Precipitation of Solid Material (S4)

The first solvent may be completely removed from the admixture, which may remain after removal of the noble metal catalyst in the previous step (S3), thus forming a precipitate or a solid material.

For example, the first solvent component (e.g., water) may be removed using a rotary evaporator, but the present invention is not limited thereto, and any method may be used, so long as water may be separated and removed from the admixture.

Separation of Precipitate (S5)

The precipitate remaining after separation of water in the previous step (S4) may be dissolved in an organic solvent. For example, when the precipitate is dissolved in the organic solvent, the undissolved precipitate remaining may be separated from the organic solvent solution.

The organic solvent may be suitably provided to the extent that a sufficient amount of the solid material may be dissolved therein. The precipitate or solid material may be dissolved in the organic solvent for a predetermined period of time until the dissolution does not occur any further, the undissolved material remaining in the organic solvent may be separated from the solution, washed with water several times, and precipitated. The remaining undissolved portion of the catalyst mixture in the organic solvent may be recovered, which may include the rhenium catalyst.

The organic solvent may suitably include acrylonitrile, which is an unsaturated nitrile material having the simplest structure, with a melting point of −83.5° C., a boiling point of 77.7° C., and a specific gravity of d20=0.806. Preferably, acrylonitrile may be used to efficiently dissolve adipic acid to obtain the adipic acid in high purity through the subsequent recrystallization.

Preparation of Particles (S6)

Acrylonitrile may be removed by, for example, vacuum evaporation, from the solution remaining after extraction and separation of the precipitate that is not dissolved in the organic solvent in the previous step (S5), thus preparing adipic acid particles.

EXAMPLE

A better understanding of the present invention will be given through the following examples, which are merely set forth to illustrate the present invention but are not to be construed as limiting the scope of the present invention.

Preparation Example

Preparation of Potassium Glucarate as Starting Material

As a starting material, glucose (hydrous glucose, Daesang, Korea) was placed at a concentration of 0.1 g/cc relative to water, serving as a first solvent component, in a reactor, and potassium hydroxide (Sigma Aldrich, USA) was added in an amount of 0.9 parts by weight based on the amount of glucose. Thereafter, a platinum catalyst (Sigma Aldrich, USA) loaded on activated carbon was added in an amount of 0.3 parts by weight based on the amount of glucose. Thereafter, the reactor temperature was maintained at 50° C., and oxygen gas was fed into the reactor such that the pressure was maintained at about 1 bar, and the reaction was allowed to progress for 4 hr. Here, the hydrogen ion concentration was maintained at a pH of 4.

After completion of the reaction, potassium glucarate, which is an organic acid in a form in which potassium ($K^+$) is bound to the end thereof, was obtained.

Figure 3:
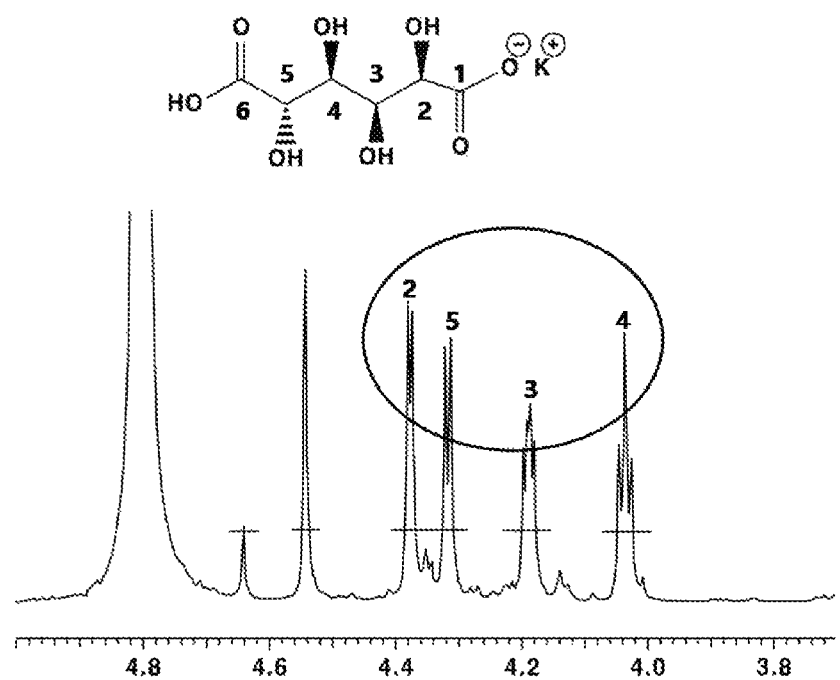
FIG. 3 is a $^1$H-NMR graph of potassium glucarate obtained by an exemplary process in the present invention.

FIG. 3 shows $^1$H-NMR data of glucaric acid. In the $^1$H-NMR graph, the peak at 4.39 on the X-axis represents the 2-position hydrogen of potassium glucarate, the peak at 4.32 represents the 5-position hydrogen of potassium glucarate, the peak at 4.19 represents the 3-position hydrogen of potassium glucarate, and the peak at 4.03 represents the 4-position hydrogen of potassium glucarate. Based on the $^1$H-NMR graph showing the peaks at the above four positions, potassium glucarate, which is an organic acid in a form in which potassium ($K^+$) is bound to one end thereof, can be found to be synthesized.

Preparation of d-glucaro-1,4:6,3-dilactone 20 g of potassium glucarate obtained in the above Preparation Example was dissolved in 100 cc of water to give an admixture, after which 40 g of an ion exchange resin (Amberlite® IR120 hydrogen form, Sigma Aldrich) was added to the admixture, followed by contact treatment for 10 hr, and the ion exchange resin particles were then removed through filtering using a filter paper.

The admixture remaining after removal of the ion exchange resin particles was added with 100 cc of 1,4-dioxane (anhydrous, 99.8%, $C_4H_8O_2$, Sigma Aldrich) and mixed with stirring for 3 hr. After sufficient stirring, the solution was frozen at a temperature of −70° C. using a cryogenic freezer and then dried for 12 hr using a freeze dryer, after which particles were obtained. The particles thus obtained were subjected to NMR (Nuclear Magnetic Resonance) to analyze the chemical structure of a desired product, from which whether a desired product was obtained was confirmed.

Figure 4:
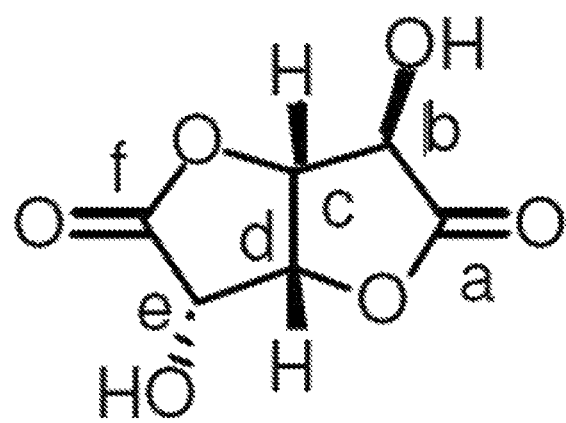
FIG. 4 is a chemical structure of d-glucaro-1,4:6,3-dilactone obtained by an exemplary process in the present invention.

FIG. 4 shows the chemical structure of the production of d-glucaro-1,4:6,3-dilactone.

The NMR results for the above chemical structures are as follows:

Respective peaks of the graph are summarized as follows.
$^1$H NMR (500 MHz, solvent: DMSO)
6.9 (br s, 1H, OHb)
6.5 (br d, J=5.2 Hz, 1H, OHe)
5.2 (dd, J=3.6, 4.0 Hz, 1JCH=170.2 Hz, 1H, Hd)
4.9 (d, J=3.6 Hz, 1JCH=168.4 Hz, 1H, Hc)
4.7 (d, J=4.0 Hz, 1JCH=144.5 Hz, 1H, He)
4.2 (s, 1JCH=156.5 Hz, 1H, Hb)
Thereby, d-glucaro-1,4:6,3-dilactone was confirmed to be produced.

EXAMPLES

Example 1

17.4 g of d-glucaro-1,4:6,3-dilactone obtained in the above Preparation Example was dissolved in 100 cc of water, and the water was sequentially added with 1.7 g of ammonium perrhenate (molecular weight: 268 g/mol, LS-Nikko Copper) and 0.8 g of a noble metal catalyst Pt—$Al_2O_3$ (Pt content: 5 wt %, Sigma Aldrich). Thereafter, the reaction temperature was elevated to about 100° C. and then maintained for 10 hr. Thereafter, hydrogen gas was introduced at 3 bar and then maintained for 2 hr. Thereafter, the reaction temperature was decreased to room temperature, and the Pt-$Al_2O_3$ catalyst was removed through filtering. Thereafter, the remaining admixture was separately collected, from which as much water as possible was then removed using a rotary evaporator, thereby recovering a solid material. The solid material was dissolved in acrylonitrile as an organic solvent, after which a solution portion and an undissolved solid portion were separated from each other. Acrylonitrile was evaporated from the solution dissolved in the acrylonitrile solvent, thus obtaining adipic acid particles. Also, the undissolved solid portion after dissolution in the acrylonitrile solvent was washed with water several times and precipitated, thereby recovering the ammonium perrhenate that was added in the initial stage of the reaction.

Examples 2 to 5

Particles were prepared in the same manner as in Example 1 under the respective conditions of Examples 2 to 5 shown in Table 1 below. The particles thus obtained were subjected to NMR (Nuclear Magnetic Resonance) to analyze the chemical structure of a desired product, whereby whether a desired product was produced was confirmed. Furthermore, like Example 1, an undissolved solid portion after dissolution in the acrylonitrile solvent was washed with water several times and precipitated, thereby recovering ammonium perrhenate that was added in the initial stage of the reaction (ammonium perrhenate is A in Tables 1 and 2 below, and the noble metal catalyst is B in Tables 1 and 2 below).

TABLE 1

| Composition | | Ex. 1 | Ex. 2 | Ex. 3 | Ex. 4 | Ex. 5 |
|---|---|---|---|---|---|---|
| Solvent | | Water 100 cc | Water 100 cc | Water 100 cc | Water 100 cc | Water 100 cc |
| d-glucaro-1,4:6,3-dilactone | | 17.4 g | 18.4 g | 19.1 g | 15.5 g | 16.4 g |
| Catalyst | A | Ammonium perrhenate 1.7 g | Ammonium perrhenate 1.8 g | Ammonium perrhenate 1.9 g | Ammonium perrhenate 1.5 g | Ammonium perrhenate 1.6 g |
| | B | Pt—$Al_2O_3$ 0.8 g | Pt—$Al_2O_3$ 0.9 g | Pt—$Al_2O_3$ 0.9 g | Pt—$Al_2O_3$ 0.7 g | Pt—$Al_2O_3$ 0.8 g |
| Reaction conditions | | 100° C., 10 hr | 120° C., 11 hr | 130° C., 12 hr | 120° C., 10 hr | 120° C., 10 hr |
| Gas | | Hydrogen | Hydrogen | Hydrogen | Hydrogen | Hydrogen |
| Gas introduction reaction conditions | | 3 bar, 2 hr | 3.5 bar, 2 hr | 3.8 bar, 2 hr | 4 bar, 2 hr | 4.5 bar, 2 hr |
| Organic solvent | | Acrylonitrile | Acrylonitrile | Acrylonitrile | Acrylonitrile | Acrylonitrile |

Comparative Examples 1 to 16

Particles were prepared in the same manner as in Example 1 using the components in the amounts shown in Table 2 below. The particles thus obtained were subjected to NMR (Nuclear Magnetic Resonance) to analyze the chemical structure of a desired product, whereby whether a desired product was produced was confirmed. Furthermore, an undissolved solid portion after dissolution of the solid material in the organic solvent shown in Table 2 below was washed with water several times and precipitated, thereby recovering the ammonium perrhenate that was added in the initial stage of the reaction.

TABLE 2

| Composition | | C. Ex. 1 | C. Ex. 2 | C. Ex. 3 | C. Ex. 4 | C. Ex. 5 | C. Ex. 6 | C. Ex. 7 | C. Ex. 8 |
|---|---|---|---|---|---|---|---|---|---|
| Solvent (cc) | | Water 100 cc | Water 100 cc | Ethanol 100 cc | Methanol 100 cc | Hexene 100 cc | Water 100 cc | Water 100 cc | Water 100 cc |
| d-glucaro-1,4:6,3-dilactone (g) | | 7 g | 30 g | 17.4 g | 17.4 g | 17.4 g | 17.4 g | 17.4 g | 17.4 g |
| Catalyst | A (g) | Ammonium perrhenate 0.7 g | Ammonium perrhenate 3.0 g | Ammonium perrhenate 1.7 g | Ammonium perrhenate 1.7 g | Ammonium perrhenate 1.7 g | — | Ammonium perrhenate 1.7 g | Ammonium perrhenate 0.6 g |
| | B (g) | Pt—$Al_2O_3$ 0.3 g | Pt—$Al_2O_3$ 1.5 g | Pt—$Al_2O_3$ 0.8 g | Pt—$Al_2O_3$ 0.8 g | Pt—$Al_2O_3$ 0.8 g | Pt—$Al_2O_3$ 0.8 g | Pt—$Al_2O_3$ 0.1 g | Pt—$Al_2O_3$ 0.8 g |

TABLE 2-continued

| | | | | | | | | |
|---|---|---|---|---|---|---|---|---|
| Reaction conditions | 100° C., 10 hr | 100° C., 10 hr | 100° C., 10 hr | 100° C., 10 hr | 100° C., 10 hr | 100° C., 10 hr | 100° C., 10 hr | 100° C., 10 hr |
| Gas | Hydrogen | Hydrogen | Hydrogen | Hydrogen | Hydrogen | Hydrogen | Hydrogen | Hydrogen |
| Gas introduction reaction conditions | 3 bar, 2 hr | 3 bar, 2 hr | 3 bar, 2 hr | 3 bar, 2 hr | 3 bar, 2 hr | 3 bar, 2 hr | 3 bar, 2 hr | 3 bar, 2 hr |
| Organic solvent | Acrylonitrile | Acrylonitrile | Acrylonitrile | Acrylonitrile | Acrylonitrile | Acrylonitrile | Acrylonitrile | Acrylonitrile |

| Composition | C. Ex. 9 | C. Ex. 10 | C. Ex. 11 | C. Ex. 12 | C. Ex. 13 | C. Ex. 14 | C. Ex. 15 | C. Ex. 16 |
|---|---|---|---|---|---|---|---|---|
| Solvent (cc) | Water 100 cc | Water 100 cc | Water 100 cc | Water 100 cc | Water 100 cc | Water 100 cc | Water 100 cc | Water 100 cc |
| d-glucaro-1,4:6,3-dilactone (g) | 17.4 g | 17.4 g | 17.4 g | 17.4 g | 17.4 g | 17.4 g | 17.4 g | 17.4 g |
| A (g) | Ammonium perrhenate 1.7 g | Ammonium perrhenate 1.7 g | Ammonium perrhenate 1.7 g | Ammonium perrhenate 1.7 g | Ammonium perrhenate 1.7 g | Ammonium perrhenate 1.7 g | Ammonium perrhenate 1.7 g | Ammonium perrhenate 1.7 g |
| B (g) | Pt—$Al_2O_3$ 0.8 g | Pt—$Al_2O_3$ 0.8 g | Pt—$Al_2O_3$ 0.8 g | Pt—$Al_2O_3$ 0.8 g | Pt—$Al_2O_3$ 0.8 g | Pt—$Al_2O_3$ 0.8 g | Pt—$Al_2O_3$ 0.8 g | Pt—$Al_2O_3$ 0.8 g |
| Reaction conditions | 50° C., 10 hr | 100° C., 10 hr | 100° C., 10 hr | 100° C., 10 hr | 100° C., 5 hr | 100° C., 10 hr | 100° C., 10 hr | 100° C., 10 hr |
| Gas | Hydrogen | Hydrogen | Argon | Oxygen | Hydrogen | Hydrogen | Hydrogen | Hydrogen |
| Gas introduction reaction conditions | 3 bar, 2 hr | 1 bar, 2 hr | 3 bar, 2 hr | 3 bar, 2 hr | 3 bar, 2 hr | 3 bar, 2 hr | 3 bar, 2 hr | 6 bar, 2 hr |
| Organic solvent | Acrylonitrile | Acrylonitrile | Acrylonitrile | Acrylonitrile | Acrylonitrile | Ethanol | Methanol | Acrylonitrile |

Test Examples

The particles prepared in Examples 1 to 5 and Comparative Examples 1 to 16 were subjected to NMR to analyze the chemical structures thereof, and the results of production of the final product, namely adipic acid, are summarized in Table 3 below.

TABLE 3

| | Example | | | | | Comparative Example | | | | | | | | | | | | | | | |
|---|---|---|---|---|---|---|---|---|---|---|---|---|---|---|---|---|---|---|---|---|---|
| Item | 1 | 2 | 3 | 4 | 5 | 1 | 2 | 3 | 4 | 5 | 6 | 7 | 8 | 9 | 10 | 11 | 12 | 13 | 14 | 15 | 16 |
| Adipic acid | O | O | O | O | O | Δ | Δ | X | X | X | X | Δ | Δ | Δ | Δ | X | X | Δ | O | O | Δ |

Evaluation criteria:

O - yield of 80% or more

Δ - yield of less than 80% but exceeding 20%

X - yield of 20% or less

Figure 5:
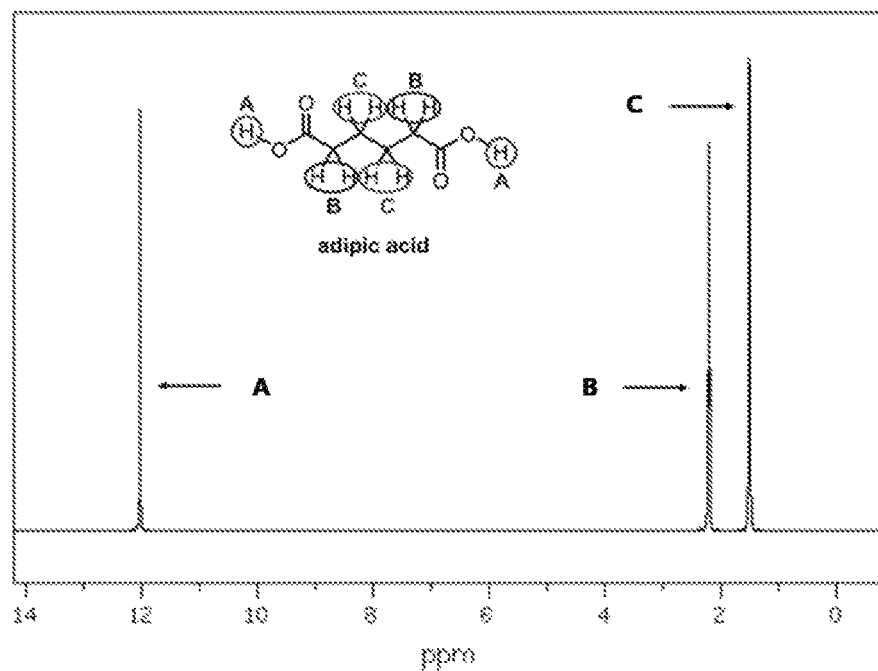
FIG. 5 is a $^1$H-NMR graph of adipic acid obtained by an exemplary process in the present invention.

FIG. 5 is a graph showing the results of confirmation of the production of adipic acid through NMR spectra. Here, NMR spectra were analyzed using a Bruker AV111400 instrument, and measurement was performed through dissolution in DMSO including TMS (trimethylsilane) as an internal standard ($^1$H at 400 MHz, $^{13}$C at 100 MHz).

Based on the results of $^1$H NMR (DMSO-$d_6$) δ 12.0 (bs, 2H), 2.23-2.09 (m, 4H), 1.52-1.48 (m, 4H), adipic acid was confirmed to be produced as a final product in Examples 1 to 5.

In Comparative Examples 1 to 16, almost none of the above peaks were observed, indicating that adipic acid could not be obtained or that the yield thereof was very low when adipic acid was obtained.

Although various exemplary embodiments of the present invention have been described with reference to the accompanying drawings, those skilled in the art will appreciate that the present invention may be embodied in other specific forms without changing the technical spirit or essential features thereof. Thus, the embodiments described above should be understood to be non-limiting and illustrative in every way.

What is claimed is:

1. A method of preparing adipic acid, comprising:
preparing an admixture comprising d-glucaro-1,4:6,3-dilactone, a first solvent component and a catalyst mixture comprising a rhenium catalyst and a noble metal catalyst;
reacting the admixture with hydrogen ($H_2$) gas;
extracting the catalyst mixture from the admixture reacted with the hydrogen gas;
forming a precipitate by removing the first solvent component from the admixture;
adding an organic solvent comprising acrylonitrile to the precipitate;
separating and removing an undissolved residue; and
evaporating the organic solvent to obtain particles comprising the adipic acid.

2. The method of claim 1, wherein the first solvent component comprises water.

3. The method of claim 1, wherein the rhenium catalyst comprises one or more selected from the group consisting of rhenium oxide, perrhenic acid, cesium perrhenate, and ammonium perrhenate.

4. The method of claim 1, wherein the noble metal catalyst comprises a metal component and a support comprising one or more selected from the group consisting of carbon, aluminum oxide ($Al_2O_3$), and silica.

5. The method of claim 4, wherein the metal component comprises one or more selected from the group consisting of platinum, rhodium, palladium, and nickel.

6. The method of claim 1, wherein the admixture comprises the d-glucaro-1,4:6,3-dilactone in an amount of about 10 wt % to 20 wt % based on the total weight of the first solvent component.

7. The method of claim 1 wherein, based on 100 parts by weight of the d-glucaro-1,4:6,3-dilactone, the catalyst mixture comprises the rhenium catalyst in an amount of about 5 parts by weight to 10 parts by weight and the noble metal catalyst in an amount of about 1 part by weight to 5 parts by weight.

8. The method of claim 1, wherein the admixture is prepared by mixing at a temperature of about 100° C. to 150° C. for a period of time of about 10 hr to 15 hr.

9. The method of claim 1, further comprising preparing the d-glucaro-1,4:6,3-dilactone.

10. The method of claim 9, wherein the d-glucaro-1,4:6,3-dilactone is prepared by steps comprising:
preparing an organic acid admixture comprising an organic acid or a salt thereof which comprises one or more potassium ions ($K^+$), wherein the organic acid is derived from a monosaccharide, and a second solvent component;
contacting the organic acid admixture on a cation exchange resin;
separating the cation exchange resin from the organic acid admixture;
preparing a composition comprising 1,4-dioxane to the organic acid admixture; and
preparing d-glucaro-1,4:6,3-dilactone particles by freezing and drying the composition, and wherein the monosaccharide is glucose.

11. The method of claim 10, wherein the organic acid or the salt thereof comprises potassium glucarate.

12. The method of claim 10, wherein, the cation exchange resin comprises a copolymer of styrene and divinylbenzene and comprises a sulfonic acid group (—$SO_3H$).

13. The method of claim 1, wherein the admixture is reacted with the hydrogen gas, by introducing the hydrogen gas at a pressure of about 3 bar to 5 bar, for about 2 hr to 8 hr.

* * * * *